United States Patent [19]

Aasberg

[11] Patent Number: 5,782,843
[45] Date of Patent: Jul. 21, 1998

[54] APPARATUS FOR IMPLANTING HAIR-ROOTS, AND A DEVICE FOR PLACING HAIR-ROOTS ON A CONVEYOR BELT FOR USE IN THE APPARATUS

[76] Inventor: Olav L. Aasberg, P.O. Box 6796, Oslo, Norway

[21] Appl. No.: 727,569

[22] PCT Filed: Apr. 25, 1995

[86] PCT No.: PCT/NO95/00067

§ 371 Date: Oct. 23, 1996

§ 102(e) Date: Oct. 23, 1996

[87] PCT Pub. No.: WO95/28896

PCT Pub. Date: Nov. 2, 1995

[30] Foreign Application Priority Data

Apr. 25, 1994 [NO] Norway .................................. 941494
Jun. 13, 1994 [NO] Norway .................................. 941494

[51] Int. Cl.⁶ ...................................................... A61B 17/34
[52] U.S. Cl. ................................................ 606/133; 606/187
[58] Field of Search ..................................... 606/187, 133

[56] References Cited

U.S. PATENT DOCUMENTS 3,596,292  8/1971  Erb .................................. 606/187 X
5,269,801  12/1993  Shiau .

FOREIGN PATENT DOCUMENTS 1953026  10/1972  Germany .......................... 606/187
1 553 950  10/1979  United Kingdom .
WO 92/00706  1/1992  WIPO .

*Primary Examiner*—Michael H. Thaler
*Attorney, Agent, or Firm*—Wenderoth, Lind & Ponack, L.L.P.

[57] ABSTRACT

A system for the mechanical implanting of hair roots into the skin has a movable magazine for receiving skin grafts. A skin graft extraction apparatus has a frame that holds a piece of skin for the supply of skin grafts in a fixed and taut manner. A cooling device cools the piece of skin. A hollow drill rod is movable between a position in which the drill rod can drill and extract the skin grafts from the piece of skin when the piece of skin is held by the frame and a position in which the drill rod can deliver the skin grafts into the magazine. An implanting apparatus is capable of receiving the movable magazine therein such that the movable magazine can be advanced stepwise therein and successively implant the skin grafts into the skin. An incision member of the implanting apparatus makes an incision in the skin, and then transversely widens the incision in the skin such that the skin can receive one of the skin grafts. An actuator rod implants the skin grafts in the movable magazine into the incision in the skin by holding a skin graft in place while a receptacle of the movable magazine is retracted. In this way, the magazine can be rapidly and automatically advanced stepwise by rapid and successive operation of the incision member and the actuator rod, thus maintaining the skin grafts in the movable magazine in the cooled state until they are inserted into the skin.

20 Claims, 13 Drawing Sheets

Detail 11A

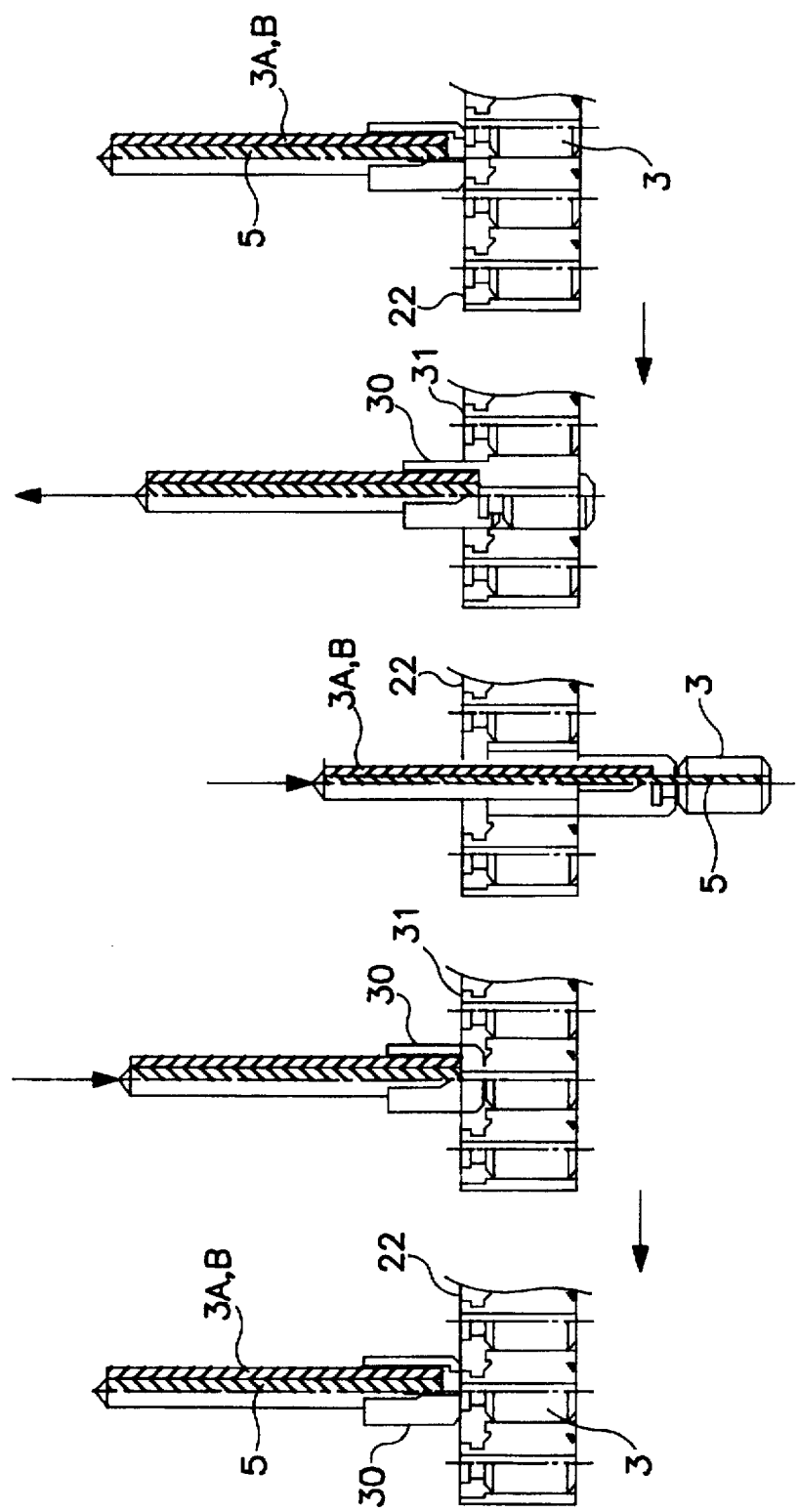

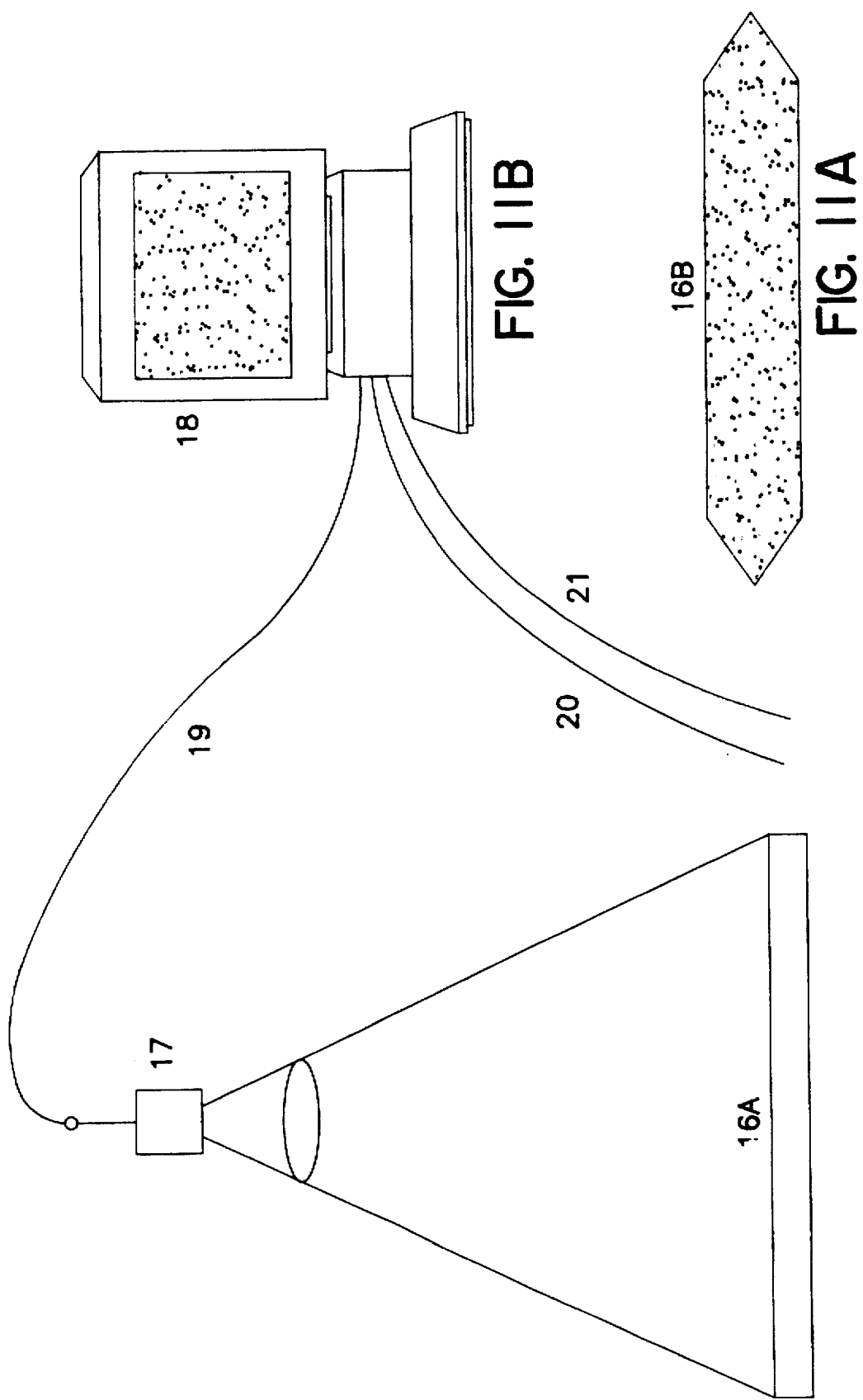

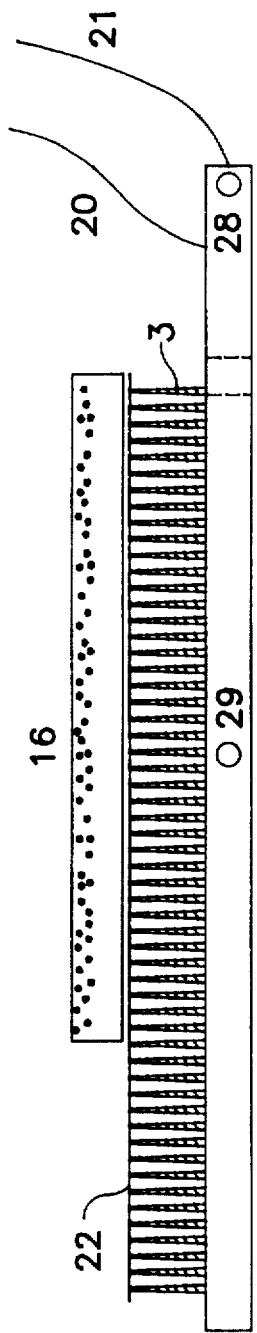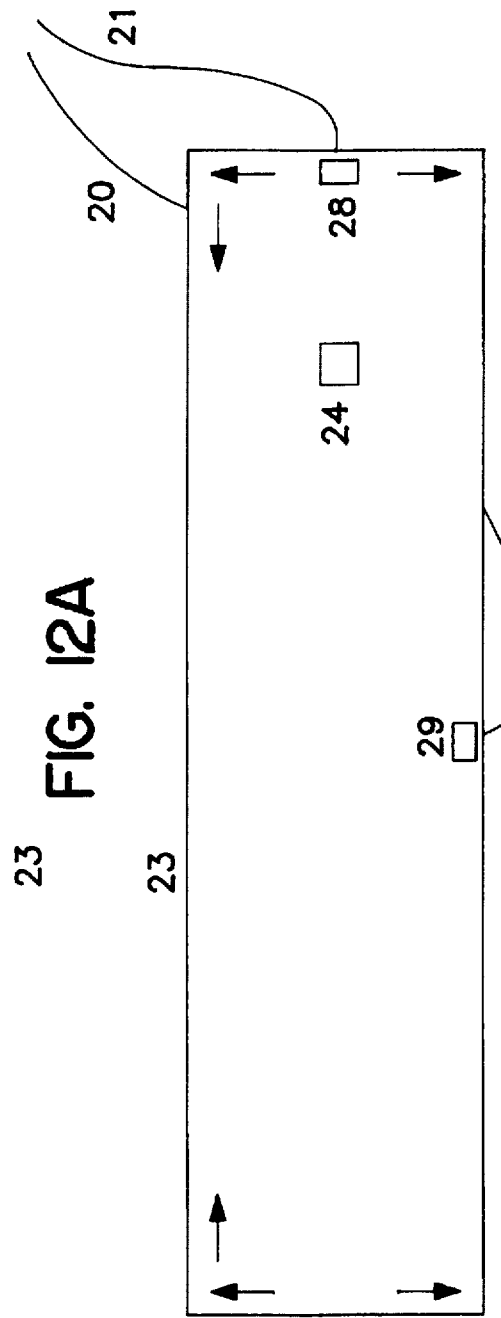
FIG. 12A
FIG. 12B

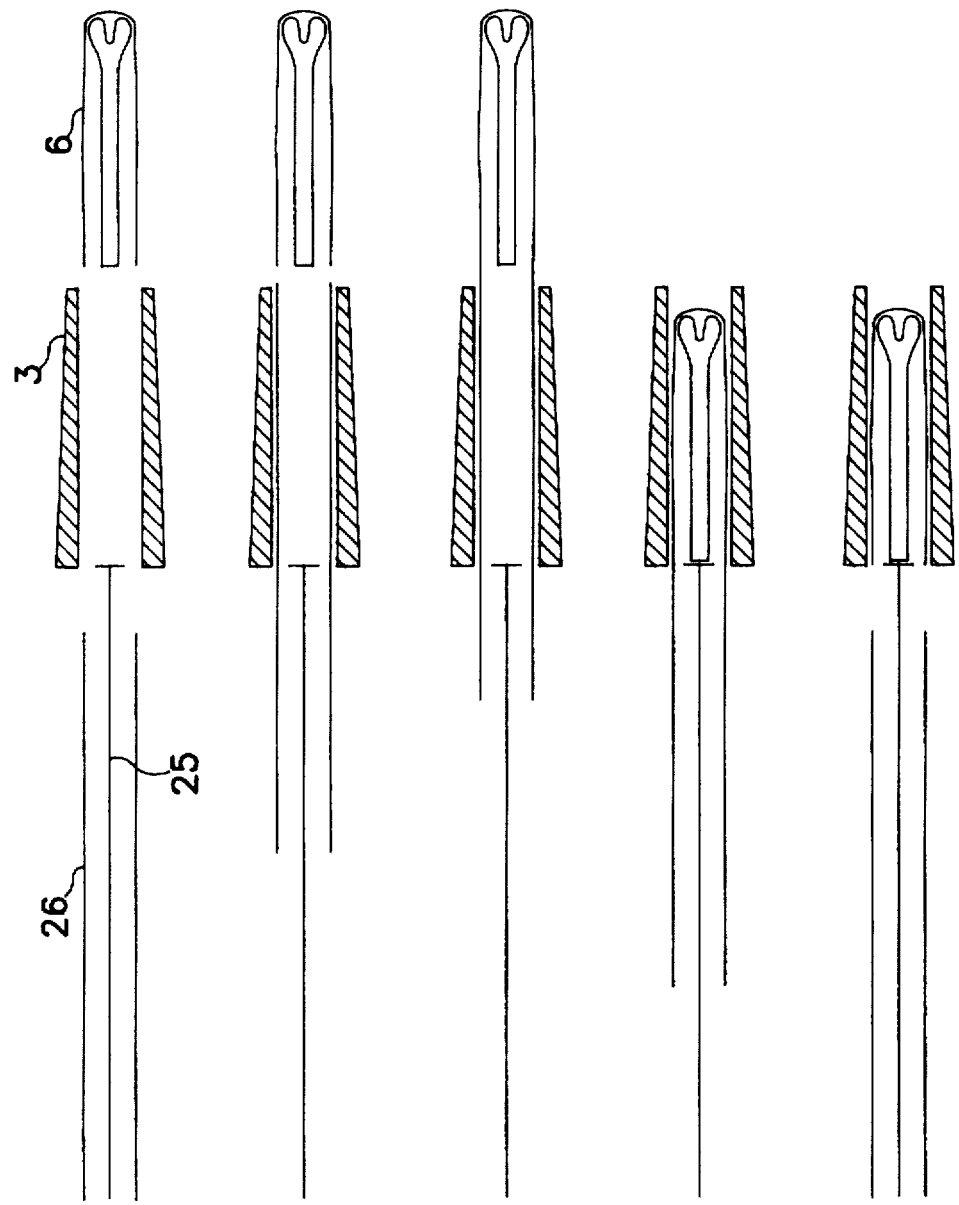

APPARATUS FOR IMPLANTING HAIR-ROOTS, AND A DEVICE FOR PLACING HAIR-ROOTS ON A CONVEYOR BELT FOR USE IN THE APPARATUS

BACKGROUND OF THE INVENTION

The present invention relates to equipment for the mechanical implanting of hair roots in skin, particularly in the head region, for use when performing transplant surgery.

There already exist several methods for making hair transplants for repair of beginning and advanced baldness, particularly with male persons, by collecting hair roots from the patient's own ear and neck areas and implanting them by hand on the bald head area. The two most common methods today include a first method where round skin patches with hair roots, so-called grafts, are collected from the ear and/or neck area. This is operation is often made by means of a cylindrical drill rod driven by a drill machine. Corresponding holes are stamped out by hand power or by using a laser in the bald area, and the transplants (the grafts) are put in place by hand, one by one.

A second method is a somewhat larger surgical operation. A larger apportioned piece of skin is cut out from the ear/neck area by means of a scalpel. The skin piece is typically elongate in shape, and taken from a neck/head area where hair growth will normally continue the whole lifetime. The skin piece is cut out in such a shape that the pulling together and sewing together of the surrounding skin will remain invisible beneath the remaining neck hair. The skin piece which has been taken out can be divided in such a manner that single hair roots or possibly larger units, i.e. grafts, can be used for implantation. The hair roots or the units can be placed in the bald head area by making small incisions with a knife, so as to split the skin, then the hair root or graft is put into place, and thereafter the skin is squeezed together again. Optionally one utilizes metal pins which are stuck into the skin. When these pins are removed thereafter, the hair roots are placed into the cavities left by the metal pins.

Both of the methods mentioned above are detailed and time-consuming.

Different types of equipment for use in such implanting operations are known, and in this connection reference is made to British patent no. 1,553,950. This publication shows a device for the mechanical implanting of hair elements where the hair is held in a tubular inner needle which at a rounded end thereof is slideably disposed within an outer needle which is rigidly secured. In the patent the outer needle is constructed in different manners, inter alia as a split-injection type, and in this case comprises a couple of arcuate knife points which are spring biased into mutual engagement at their relatively sharp and mutually supporting ends. The mode of operation is that the outer needle cuts into the skin, and then the inner needle holding the hair element to be implanted follows down into the cavity made by the outer needle. When the outer needle is pulled back, the inner needle remains standing in the skin to hold the hair element, and the inner needle is pulled out last, while the hair element is then held by the skin which collapses around the hair element. When the outer needle is of the split-injection type, the knives are split apart after having entered the skin in order that the inner needle may advance in between the two sharp knives, which are thereafter retracted.

However, the above mentioned GB 1,553,950 relates to implanting hair elements without hair roots, i.e. instead of using real hair roots, which roots will continue generating new hair in a normal manner, one implants hair by simply making a loop in the lower part, and one then hopes that this loop shall get a foothold in the skin, and further it is hoped that the hair element shall last as long as possible. Such an implanting operation is in principle quite inferior when compared to a transplantation of a hair root which will provide genuine hair growth in the years to come. Also, the previous publications mentioned in GB 1,553,950 relate to techniques of implanting hair elements, not hair roots. Nevertheless, in the present invention a technique is used which is similar to the technique used in GB 1,553,950, which thus represents the closest prior art known to the inventor of the present invention.

SUMMARY OF THE INVENTION

The present invention aims at providing equipment which increases the degree of mechanization in hair root transplant operations, and also aims, as a further favorable effect, at shortening the time that the patient has to wait for full-grown, durable hair of acceptable length. It is actually an additional known problem that when transplanting hair roots, one has to wait about 8–12 weeks for the visibility of the new hair, since the transplanted hair roots receive a shock during the long treatment time.

The above mentioned aim, namely achieving a transplanting operation which can be accomplished faster, is achieved by providing equipment which comprises an apparatus for the mechanical implanting of hair roots, as well as a device for placing grafts (small skin pieces) on an assembling strip adapted to be used in the apparatus, where the equipment satisfies the following conditions.

The apparatus of the invention for mechanical implanting of hair roots in skin by insertion of grafts (small skin pieces), each graft comprising at least one hair root, has a forward facing front section with at least one incision member adapted to incise into the skin under pressure from behind in order to make at least one opening in the skin to allow insertion of at least one forwardly and rearwardly open and substantially cylindrical receptacle containing a graft, and thereafter to return together with the receptacle while leaving the graft in the skin. The apparatus is characterized in that it is designed like a pistol, with a muzzle from which the incision member and the receptacle can be forced rapidly forward and into the skin. The receptacle is at the start provided on an assembling strip or a magazine for a plurality of such receptacles. The assembling strip can be conveyed through a transverse opening at the muzzle immediately behind the retracted incision member position for successive dispensing of receptacles. The assembling strip advances at least one receptacle position automatically after each new graft implanting.

The pistol further comprises regulator-driven actuator rods adapted to drive, in controlled succession, at least one receptacle containing a graft, as well as the incision member, rapidly forward from the assembling strip and into the skin, and to retract the receptacle and the incision member in correspondingly controlled succession. A centrally located actuator rod for moving the graft only is adapted to be retracted last in the succession, so that a graft which has been inserted is retained by the surrounding skin tissue.

The incision member of the apparatus preferably comprises two pointed knives arranged closely together adapted to be is split apart after incision in the skin in order to allow insertion of the receptacle between the knives.

Further, the centrally located actuator rod can be rotatable about its own longitudinal axis, whereby the graft can be detached more easily from the forward end of the actuator rod in connection with the retracting operation.

An actuator rod for moving the receptacle can be equipped with engagement details in its forward end for cooperation with corresponding engagement details on the rear end of the receptacle so as to enable receptacle retraction.

In accordance with the invention the equipment further comprises a means for placing grafts (small pieces of skin), each comprising at least one hair root, onto an assembling strip or magazine. The assembling strip is adapted to be used in the above mentioned apparatus for implanting grafts/hair roots. The means comprises a) a frame for fixed positioning of a larger piece of skin which has been surgically cut out from a hairy head area, the frame also comprising a device for cooling the piece of skin.

b) a videocamera for viewing the piece of skin and smaller areas thereof, c) a computer, including a monitor, for receiving video signals from the camera, presentation of the picture on the monitor, and calculating the position of the single hair roots on the piece of skin, d) a table positioned adjacent to the frame, which table is movable in two orthogonal directions relative to the frame by means of two motors and is controlled by the computer, e) a drill with a thin and hollow drill rod having an inner diameter which defines the graft diameter, the drill being located in a fixed position on the table in such a manner that the drill rod can be run forward and backward through the skin piece at right angles to both of the orthogonal directions, the drill motor being started and stopped under control of the computer, f) a conveyer belt connected to the table, whereby the drill rod in operation can pass immediately above the conveyer belt before or after piercing the skin piece, the conveyer belt carrying an assembling strip or magazine on which a plurality of substantially cylindrical receptacles which are open in both ends have been placed beforehand, so that the drill rod in operation can pass through a receptacle, the conveyer belt being stepwise movable past the drill rod position under control of the computer, and g) a center rod positioned centrally inside the drill rod to stop the graft in a position inside a receptacle after extraction of the graft from the skin piece, since a graft will adhere to the inside of the drill rod after having been drilled out due to friction.

Preferably the computer is adapted to coordinate the operation of the motors for relative movement between table and frame, the drill motor, the advancement of the drill rod and the conveyer belt in such a manner that the assembling strip is advanced one receptacle position or a given number of receptacle positions between every drill/drill rod extraction cycle, and in such a manner that an extraction cycle is started when the drill rod is in a correct position in alignment with a hair root or a number of hair roots to be comprised by a graft, as determined by the computer positioning and regulated by means of the motors for relative movement.

Preferably the frame is adjustable in a tilted direction so that the drill direction can be brought to optimum coincidence with the general direction of the longitudinal axis of the hair roots.

Preferably the frame is also equipped with two rows of slanted needles for mounting the skin piece. Each needle row is mounted on the edge of two plates which can be forced apart by means of a spring or screw device so that the skin piece is tightened and pulls itself down to a position in a well defined plane in the frame before starting the extraction operation.

The cooling device preferably comprises controllable supply hoses for cooled air adapted to blow air toward the piece of skin.

In one embodiment of the means according to the invention, the table having a drill with a drill rod mounted thereon, as well as the conveyer belt, are located on one side of the frame holding the skin piece, while the videocamera is placed on the opposite side of the skin piece, whereby the conveyer belt holding the assembling strip and receptacles is located between the drill and the skin piece. The drill rod moves through a receptacle prior to hitting the piece of skin, and after drill-out carries the graft back into the receptacle. The center rod stops the graft inside the receptacle while the drill rod is further retracted out through the receptacle.

In this embodiment the table is preferably equipped with lamps and possibly mirror devices to illuminate the skin piece in such a manner that the videocamera views the skin piece by means of transmitted light.

In another embodiment of the means in accordance with the invention, the frame is positioned between the drill and the conveyer belt, and is controllably movable in a direction transverse to the drill rod run direction in order to remove the frame intermittently from the table with drill and conveyer belt. The drill rod is run forward to drill a graft out of the skin piece, and thereafter retracted containing the graft. The frame is moved away in a transverse direction. The drill rod advances again to enter a receptacle on the assembling strip, and the center rod then stops the graft inside the receptacle when the drill rod is retracted once more. Finally, the center rod is thereafter also returned to make room for driving the frame back to a new controlled position for extracting a new graft, the frame being controllably movable also in a second direction orthogonal to the drill run direction.

In the last mentioned embodiment the videocamera and an illumination device are preferably provided on respective sides of the frame where the frame stops in its removed position for determining desired drilling positions in the skin piece before moving the frame back to the extraction position.

In an embodiment where it is desirable to have a rapid extraction of grafts, the drill is adapted for simultaneous operation of a number, for example five, of parallel placed drill rods with adapted axial spacings equal to the center axis spacing between two neighboring receptacles on the assembling strip/magazine for rapid extraction of a number of grafts in one operation. These grafts are placed in the same number of receptacles on the assembling strip/magazine. The computer controls the operation in this case, regarding displacements and consecutive order, while the positions for extracting grafts from the skin piece are merely determined as matrix positions, and the parallel placed drill rods are shifted in a transverse direction from one drill operation to the next.

In the process of mechanical implanting of hair roots using the equipment of the present invention, the process to be executed will be more mechanized and substantially faster than what has previously been possible. The previously used method of cutting out skin pieces in the neck and ear region is maintained, but when such a skin piece has been placed in the specially constructed frame, the hair roots will be extracted rapidly from the skin under the control of a computer and placed directly in receptacles an assembling strip. From this strip the receptacles can thereafter be shot directly into the skin of the patient by means of a specially constructed pistol. The specially made assembling strip or magazine is placed in a specially constructed opening in the pistol, and the hair roots or grafts can be shot directly into the skin consecutively until the assembling strip is empty. Such an operation can be executed very much faster than corresponding previous operations.

The feature of a cooling device in connection with the frame in which the skin piece is mounted in a taut fashion ensures that the fat surrounding the hair roots stiffens, and is hence the drilling operation is made easier. By cooling the skin in the donor area in the neck already prior to removing the skin piece, and by holding the cut-out piece of skin under constant cooling in the frame until the single hairs or grafts are shot into the skin, one also obtains the essential effect that the previously mentioned transplantation shock is avoided, and the possibility of a more rapid growth of new hair increases considerably.

BRIEF DESCRIPTION OF THE DRAWINGS

The invention will now be described in more detail with reference to a preferred embodiment and to the appended drawings, where:

FIGS. 12(a) and 12(b) show side and plan views, respectively, of a table for positioning an assembling strip relative to a skin piece, FIG. 13 indicates substantially the same situation as shown in FIG. 12, however with a drill machine and a drill rod drawn on the table, FIGS. 14(a)–(e) show successive phases of a drill-out operation of a hair root from a skin piece, FIGS. 15(a) and (b) show an embodiment of a means for placing grafts on an assembling strip, where a frame holding the skin piece can be moved away from an assembly of a drill and an assembling strip on the table, and where a drill comprising a drill rod and the assembling strip are placed on respective sides of the frame with the skin piece.

DETAILED DESCRIPTION OF THE PREFERRED EMBODIMENTS

Figure 1:
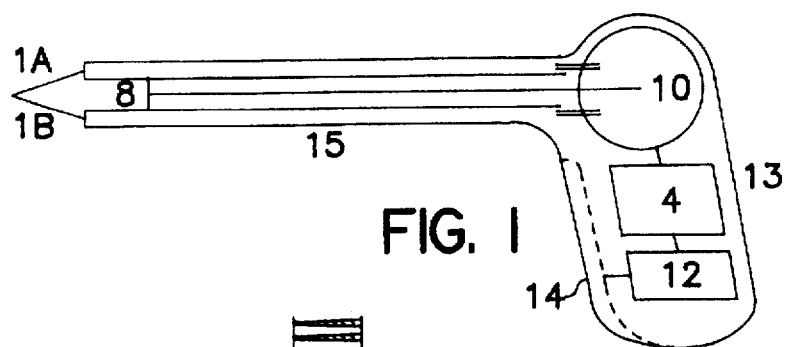
FIG. 1 schematically shows a construction of a hair shoot-in pistol in accordance with the invention.
Figure 2:
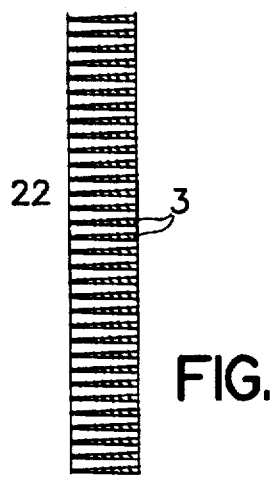
FIG. 2 shows an assembling strip or magazine with a number of receptacles for the intermediate storage of hair roots or grafts.

FIG. 1 schematically shows the general layout of an apparatus in accordance with the invention for the mechanical implanting of hair roots into skin. The apparatus is shaped substantially like a pistol, and in the forward end of the barrel 15 two pointed knife blades 1A, 1B are shown. These knife blades are forced into the skin by means of mechanisms which appear in more detail in FIGS. 3–6. These mechanisms are actuator rods adapted to push both these knife blades and further elements rapidly forward in controlled succession. In a grip or handle section 13 of the pistol, behind a barrel 15, is arranged a trigger means 14 for releasing power. The trigger influences the power supply section 12, which may be a battery or some other type of supply of electrical current. A regulator 10, which influences the various actuator rods passing through the barrel, is controlled via an electronics member 4. In the forward part of the barrel there is an opening 8 for conveying therethrough an assembling strip 22 which is shown in FIG. 2. The assembling strip 22 carries a number of substantially cylindrical receptacles 3, each containing one or several hair roots. An advancement means, not shown in the drawing, provides advancement of the assembling strip receptacle position between every shot discharge.

Figure 3:
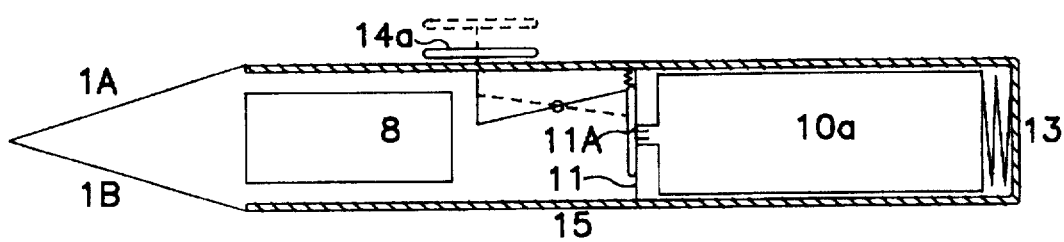
FIG. 3 shows in closer detail an embodiment of certain features of a shoot-in pistol in accordance with the invention.
Figure 4:
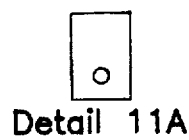
FIG. 4 shows a detail of FIG. 3 in side view, FIG. 5 schematically shows a corresponding embodiment of the pistol of the invention as shown in FIG. 3, but with emphasis on other details.

In FIG. 3 is shown a somewhat more detailed, and to a certain degree different, embodiment of the pistol of the invention than what appears from FIG. 1. The forward knives 1A, 1B and the opening 8, as well as the indication of the barrel 15 and the rearward handle 13 are as indicated in FIG. 1, but reference numeral 10a indicates in this case an air cartridge containing high-pressure air. A trigger mechanism 14a opens an air inlet to pressure hoses shown in FIG. 5. An opening in a separating wall 11 can be brought into coincidence with a hole in an opening disk 11a by operating the trigger 14a. The opening disk 11a is shown in detail in FIG. 4.

It is to be noted that instead of the pressurized-air cartridge 10, the pistol can be provided with a direct hose connection to a compressor which provides a high pneumatic pressure for use in the above mentioned pressure hose.

Figure 5:
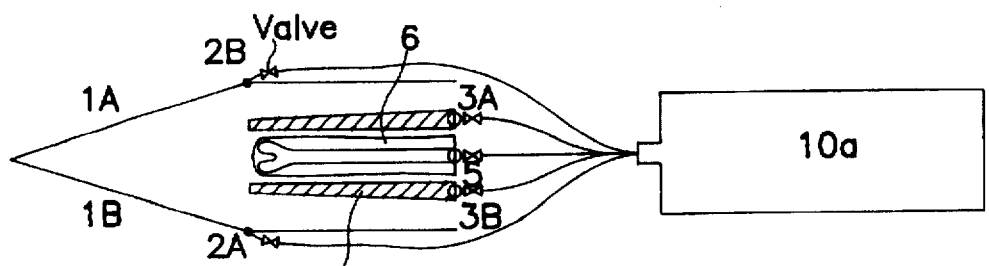

In FIG. 5 are shown separate pressure transmission hoses to the separate actuator rods which drive respective knives 1A and 1B (actuators 2A and 2B), receptacle 3 (actuators 3A, 3B) and hair root 6 (actuator 5) forward via computer controlled valves, which rapidly and successively regulate the pressures for the various actuators so as to obtain a controlled operation.

Figure 6:
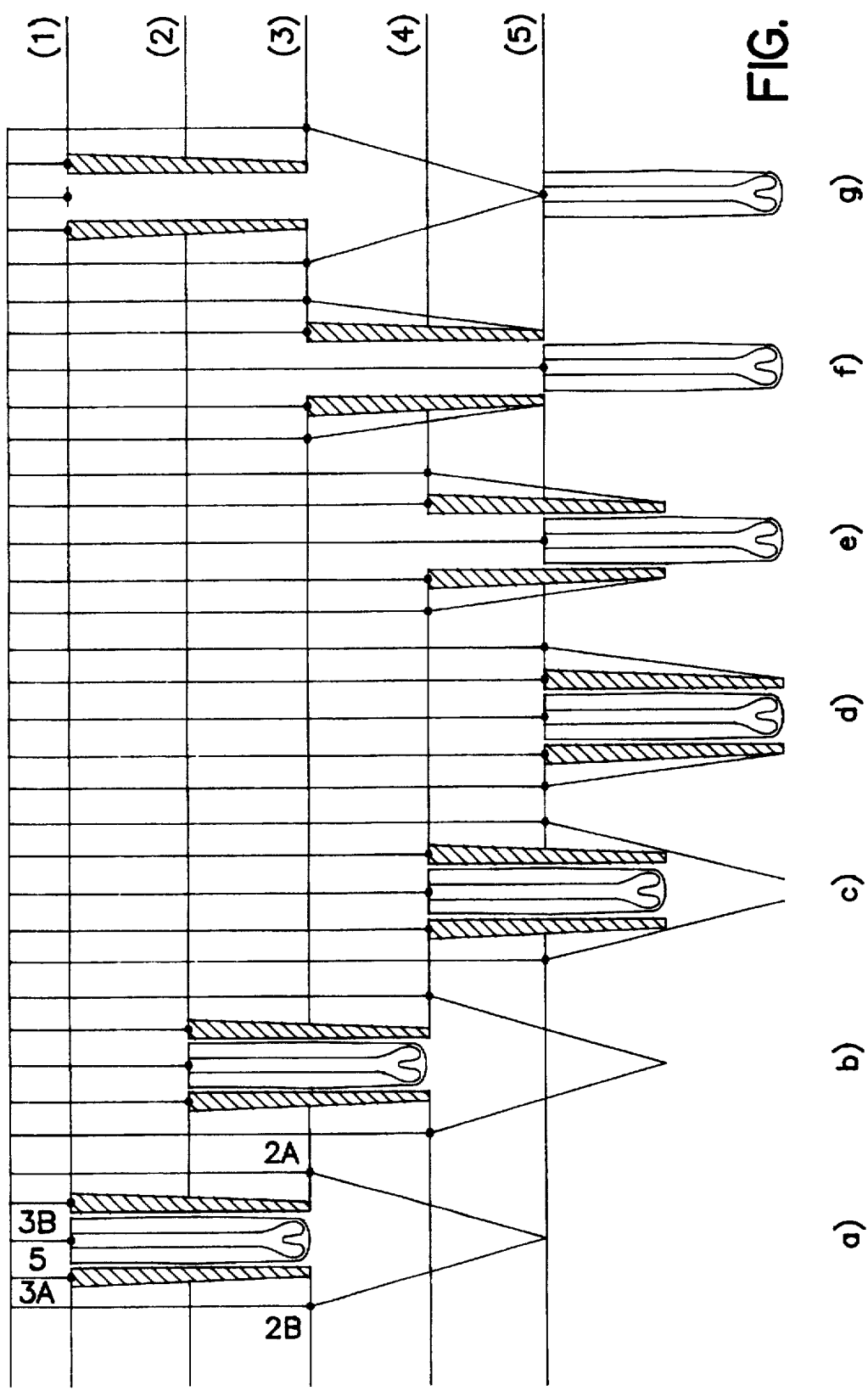
FIG. 6 is a schema showing successive movements in a forward part of the pistol of the invention during a hair shoot-in operation.

FIG. 6 shows successive positions for the forward parts of the pistol of the invention during a hair root shoot-in process. In the situation (a) to the far left, a receptacle containing a hair root lies ready right behind the knife points. In situation (b) the knife points are an their way into the skin, and the receptacle containing the hair root follows. In situation (c) the knife points have penetrated as far into the skin as necessary to plant a hair root at a sufficient depth; the receptacle containing the hair root has advanced further.

and in this situation it forces the knives a little apart. In situation (d) the receptacle has been forced equally as far into the skin as the knife points, and thereby the knife points have been forced sideways. The hair root has been advanced equally far. In situation (e) the knife points and receptacle are retracted simultaneously, while the actuator rod 5 (see reference numeral 5 shown in situation (a)) still holds the hair root in place, so that it does not accompany the receptacle in the retracting motion. In situation (f) the same motion has continued, and the knife points have reached their original position, but are still spread out due to the receptacle. What happens next is that the central actuator rod 5 is retracted rapidly to the position shown in situation (g), namely right behind the original position of the receptacle. In order to avoid that the central actuator rod pulls the hair root back again, and to let go of the hair root, it may be favorable for the rod to be given a rotation about its longitudinal axis just before it is retracted. Immediately thereafter the receptacle is retracted to its original position, which entails that the knife points clap together again to their normal position. The hair root is now inserted in the skin, which rapidly collapses around the hair root to retain it in its position, and the assembling strip advances one step so that a new receptacle containing a hair root is laid ready for the next shoot-in.

Figure 7:
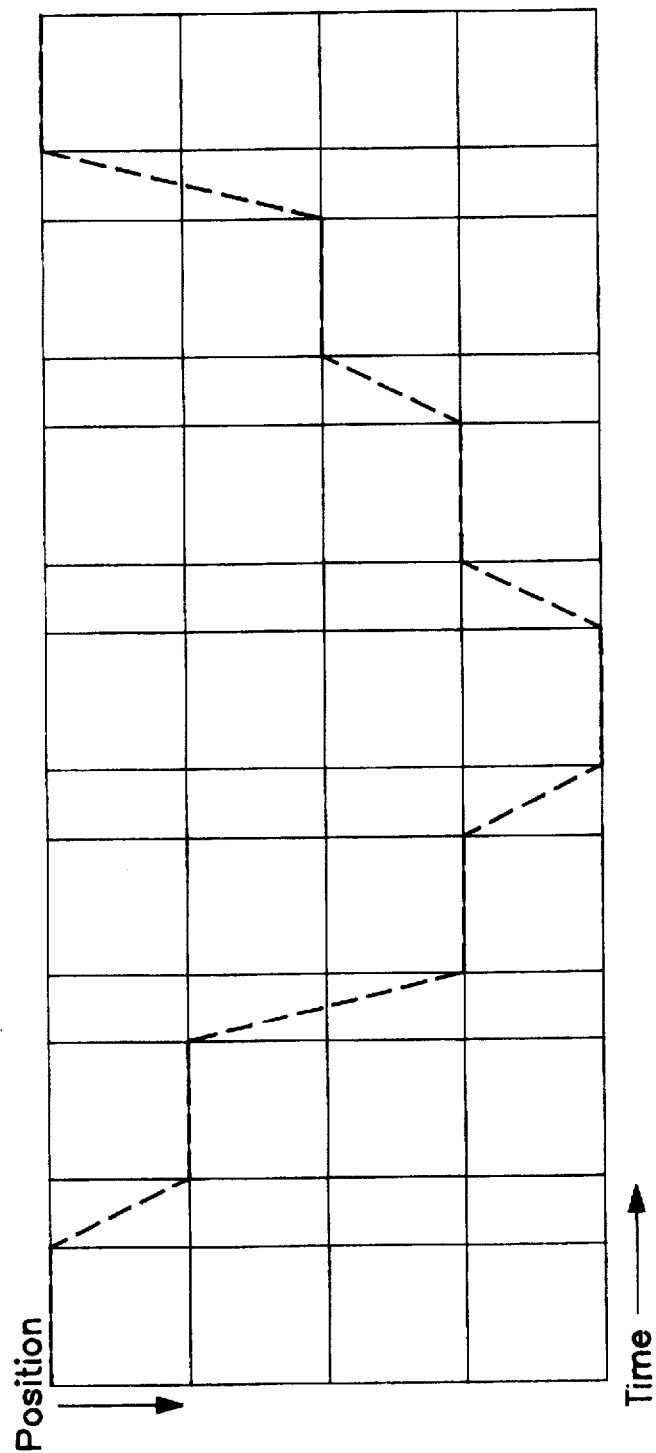
FIGS. 7–9 show programming charts for displacement of various details in the forward part of the pistol during an implanting operation, FIGS. 10(1)–(5) shows an operation sequence and details in the forward part of the pistol and in the hair root receptacles which will ensure a possibility for retracting a receptacle after having shot it into the skin, FIGS. 11(a) and (b) schematically show a set-up of a videocamera for viewing a tautly mounted skin piece, as well as a camera connection to a computer and a monitor included in a means for placing grafts on an assembling strip, where a movable table with a drill, and an assembling strip with receptacles are located on one and the same side of a frame with a tautly mounted skin pieces.
Figure 8:
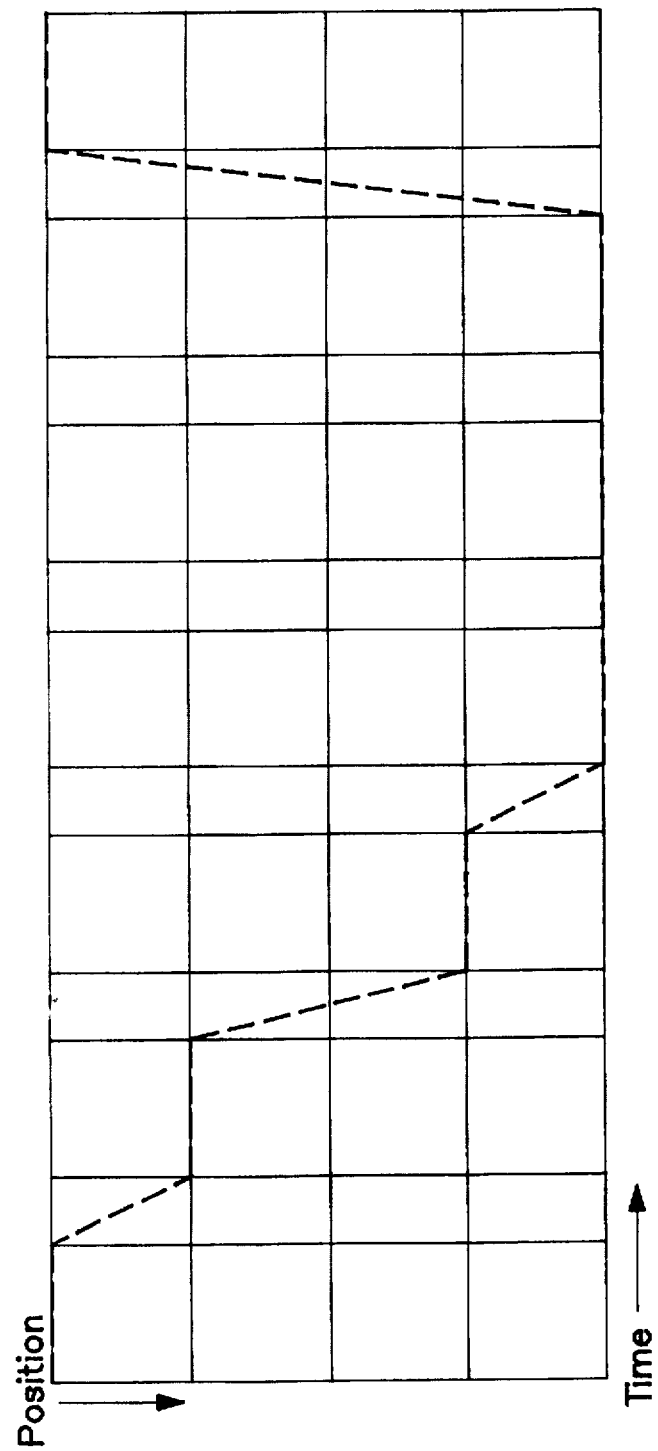
Figure 9:
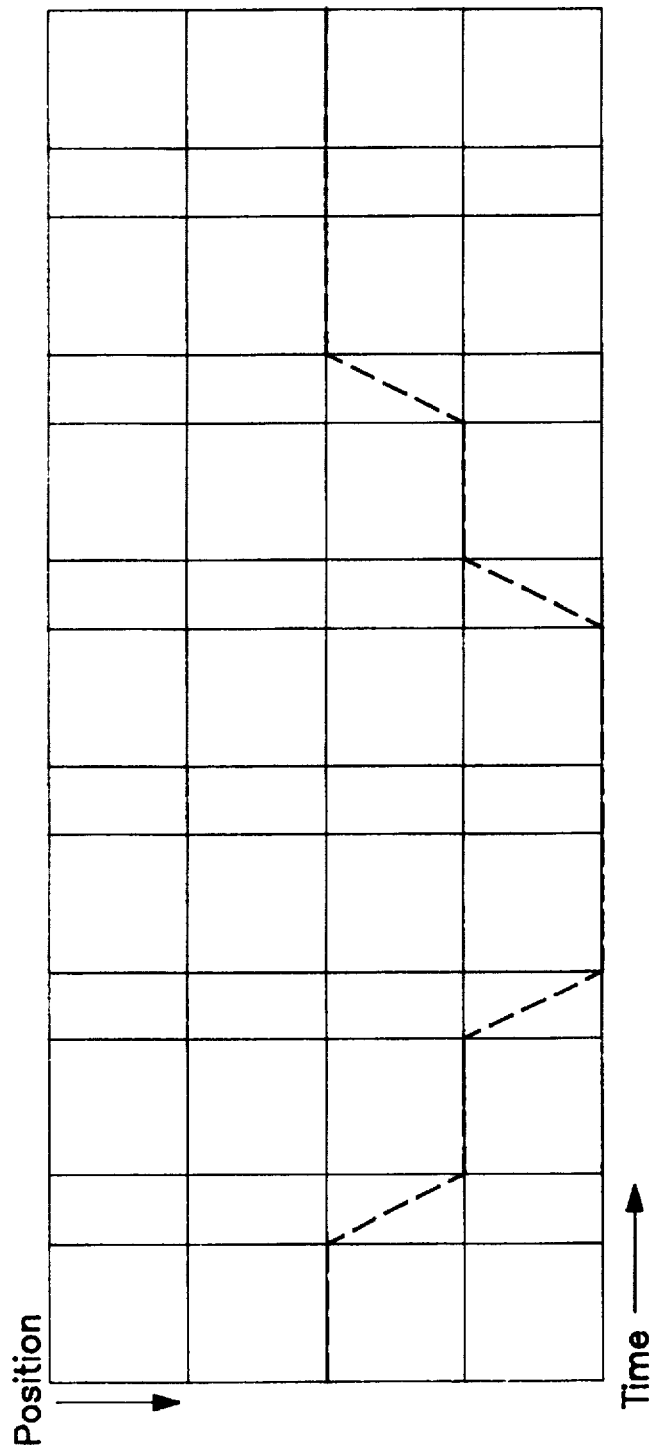

In FIGS. 7–9 are shown programming schemes for moving the actuator rods for, respectively, the receptacle 3, the hair root or the graft 6, and the incision members 1a, 1b in the implanting operation. These programming schemes correspond to what appears in FIG. 6. The time factor for the various movements can in principle be regulated mechanically or electronically.

In order that the receptacle 3 shall be retractable by the actuator rod 3A, B, it is necessary to have a special design for both of these elements. FIG. 10 shows an operation wherein substantially cylindrical receptacles 3 are used, however these receptacles are provided at the rear end (the top end) thereof with an edge 31 above a narrower part such that a gripping sleeve 30 can be snapped over the edge 31 when the actuator rods 3A, B and 5 are moved downward. Note the transition from situation 1 to situation 2. In situation 3 the receptacle has been moved down into the skin (the knives 1A, 1B are not shown in this sketch), and in situation 4 the receptacle is about to be pulled up to its place in the assembling strip 22. In situation 5 the actuator rods have been pulled further up, so that the gripping sleeve 30 has been released, and the assembling strip 22 is now about to advance one position ahead.

FIGS. 11–17 relate to that part of the equipment which is used in the introductory part of the transplanting operation, namely in the process of extraction of hair roots or grafts from a cut-out piece of skin 16, which is shown in FIG. 11(a) from above as reference 16B and in FIG. 11(b) as a side view as reference 16A. As appears from FIGS. 11, the skin piece 16 is viewed by a videocamera 17, which camera delivers video signals 19 to a computer which is adapted to analyze the video signals and at the same time present the video picture by means of a monitor 18. The computer is also adapted to control motors, symbolized by means of leads 20 and 21.

The skin patch 16 is initially fixed in a taut manner so as to be in a plane, and so as to be brought into sharp focus for the videocamera 17. By means of transmissive illumination, the single hair roots will be clearly visible in the video picture, due to the fact that the hair roots are darker than the layer of fat surrounding them, and hence a sufficient contrast is obtained.

Figure 13:
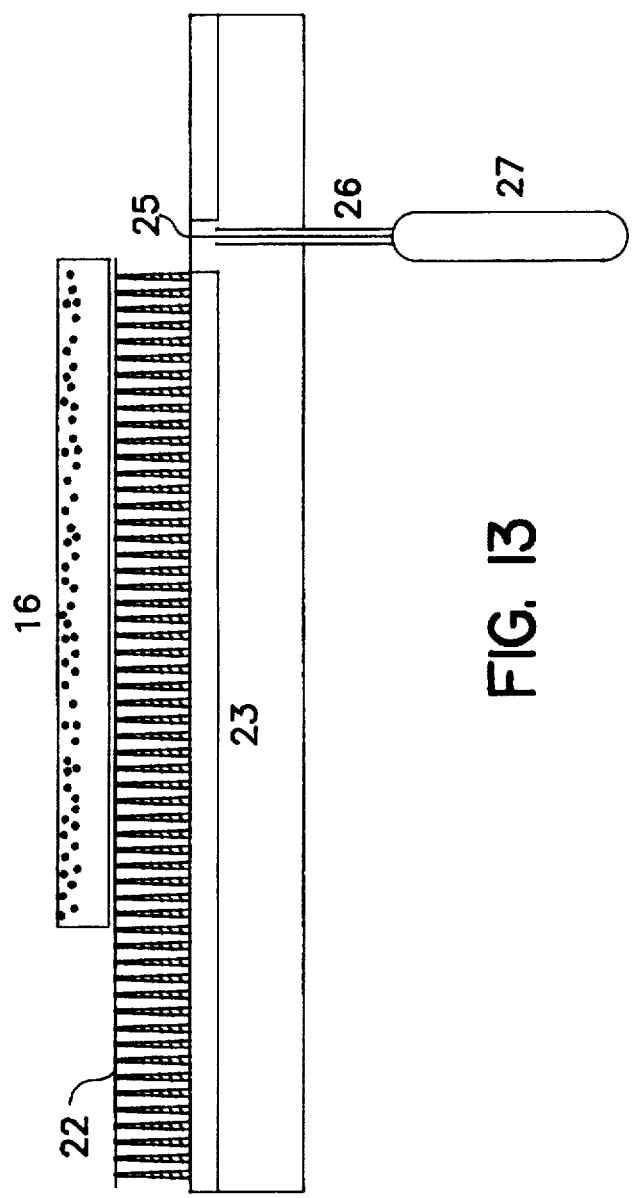

FIGS. 12 and FIG. 13 show substantially the same configuration of an arrangement of a skin piece 16, which is viewed toward the edge thereof held in a frame (not shown, a frame will appear in FIG. 17, which is dealt with later). In FIG. 12(a) there is an assembling strip 22 comprising a number of receptacles 3, which receptacles are empty in the beginning, positioned just in front of the skin piece 26. The assembling strip 22 is movable on a conveyer belt with a motor which is also controlled (not shown) from the computer. Thus, the assembling strip can be moved stepwise in the right-left direction. The table 23 is movable by means of motors 28 and 29, which motors are able to displace the table 23 in two mutually orthogonal directions. The table has a hole 24, and in connection with the hole 24 there is an arrangement as shown in FIG. 13.

In FIG. 13, a drill 27 has a motor for rapid rotation of a hollow drill rod 26 having a sharp and circular forward edge. This drill rod is adapted to advance forwardly through the hole 24, further through a receptacle 3 which has been stepped forward to a position in front of the hole by driving the assembly strip 22 to the right, and thereafter the drill rod 26 advances further into and right through the skin piece 16. The position for perforating skin piece 16 is determined by the computer, so that the hole is drilled exactly around one hair root, or possibly around a number of hair roots, constituting a graft. When the drill rod 26 has penetrated right through the skin piece, the drill rod contains the graft in question, which graft will go with the drill rod when the rod is retracted due to friction against the inner wall of the drill rod. A center rod 25 in the middle of the hollow drill rod is placed in such a manner that it stops the graft and releases it from the drill rod when the drill rod is retracted out of the receptacle. Hence the extracted graft will remain inside the receptacle 3. When a receptacle 3 has been filled with a graft, the assembling strip 22 will be stepped one position forward. The table 23 is set to a correct position for extracting a new graft, using motors 28 and 29, and thereafter the drill rod 26 will advance once more through the next receptacle in order to extract the next graft in a corresponding manner.

In such a manner the assembling strip 22 will be filled automatically in cooperation with the videocamera and the computer, and can after such a rapid filling be placed into the previously mentioned pistol for shooting grafts/hair roots into the skin of the bald area of the patient.

The above mentioned extraction operation is further explained in FIG. 14, in which figure one sees clearly, in succession from the top downwards, how the center rod 25 always stands still at the rear edge of the receptacle while the rapidly rotating and cylindrical drill rod 26 moves through the receptacle and cuts in through the skin piece to surround the graft/hair root in question. Thereafter the rod 26 brings the hair root/graft back due to the friction, and finally the graft is retained inside the receptacle by the center rod 25. It should be noted here that cooling of the skin patch 16 causes the graft which is drilled out to stay rather stiff and to be easily manageable as a unit, such as shown in the drawings.

Figure 15B:
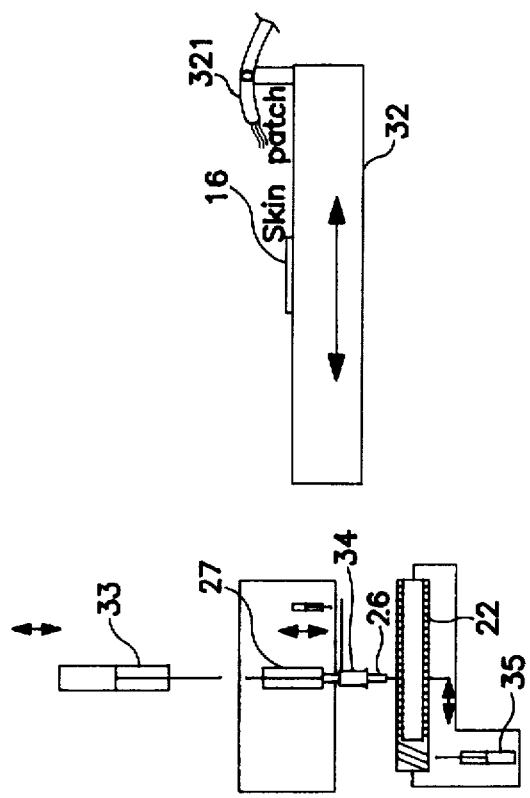
Figure 15A:
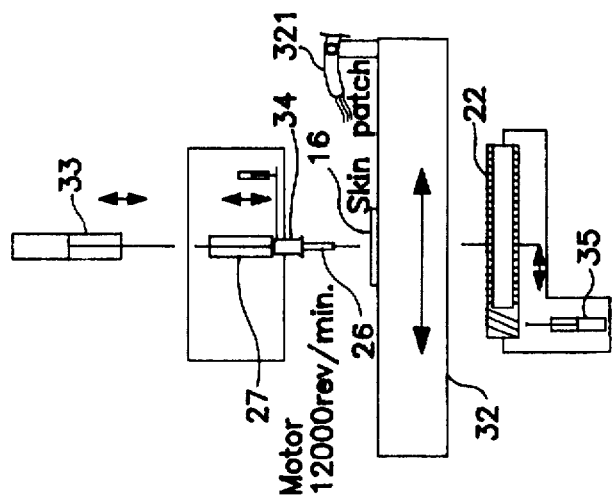

In FIGS. 15 appear an alternative embodiment of the set-up for extraction of hair roots/grafts from the skin patch 16. The skin patch 16 is shown schematically to be fixed to a frame 32, and it is shown from the difference between the two FIGS. 15 (a) and (b) that frame 32 is movable in a direction out to the right, such as shown in FIG. 15(b), in relation to the remaining devices shown. A table, not shown, which supports the remaining elements, is "standing still" while the relative movement between the frame and the table is provided by movement of the frame 32. The main reason for the variant shown here, is that it is simpler to obtain a satisfactory viewing situation for the videocamera with transmissive illumination in a situation like the one shown in FIG. 15(b). Thus, in the 15(b) situation, the desired position in the skin piece 16 for extracting a graft can be properly determined. Using mechanically stable and precise guides, exact drilling can still be made when the frame 32 carrying the skin piece 16 has been returned to the position indicated in FIG. 15(a).

Thus, in this variant, the assembling strip 22, which can be advanced stepwise in a corresponding manner as previously mentioned by means of the motor 35, which is also governed by the computer, is positioned on one side of the frame carrying the skin piece 16, while the drill 27 and the cylindrical drill rod 26 are placed on the other side of the frame 32 with the skin piece 16. Reference numeral 33 refers to an advancement mechanism which is also controlled by the computer. Programming is provided for in the following manner. After having determined a position for the extraction of a graft, the is cylindrical drill rod 26 advances in through the skin patch 16 in the same manner as previously mentioned. Thereafter the drill rod is retracted while containing a graft. Then frame 32 is moved out in a direction to the right for viewing by the videocamera and determination of a new extraction position, while at the same time the section comprising the drill rod 26 advances further, i.e. "downwards", to a receptacle on the assembling strip 22. In order to put the graft in a receptacle, a center rod is shot forward by means of the indicated mechanism 34, so that when drill rod 26 is retracted again, the graft will remain in the receptacle. Thereafter, the assembling strip 22 is shifted one position, the complete "upper" assembly moves back up to its start position, and frame 32 slides in to a new position as determined by the video viewing which has just been executed. Thereafter the operation is repeated.

As previously mentioned, this alternative can be used to provide improved illumination in the video viewing, which part of the process can be somewhat problematic in the previously mentioned case. In the previously mentioned case, illumination means, i.e. lamps and possible mirrors, must be arranged in somewhat squeezed positions between the table 23 and the frame carrying the skin piece 16.

Figure 16A:
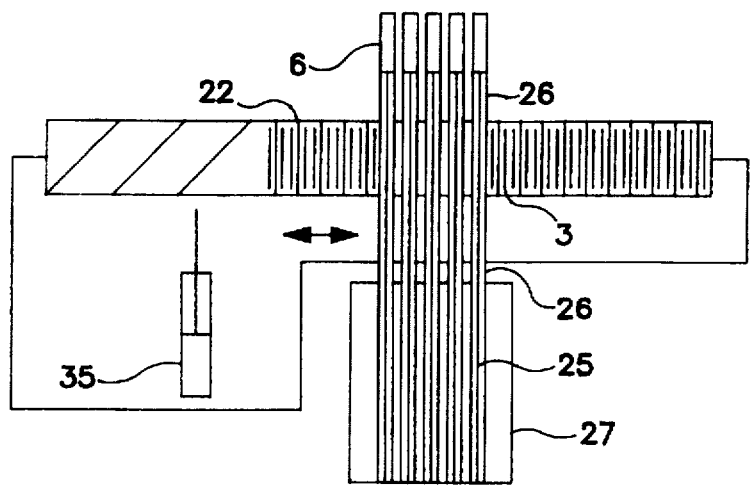
FIGS. 16(a)–(c) show successive phases of a drill-out operation from a skin piece using five parallel drill rods, and FIGS. 17(a) and (b) show a frame for mounting a cut-out piece of skin in a taut fashion.
Figure 16B:
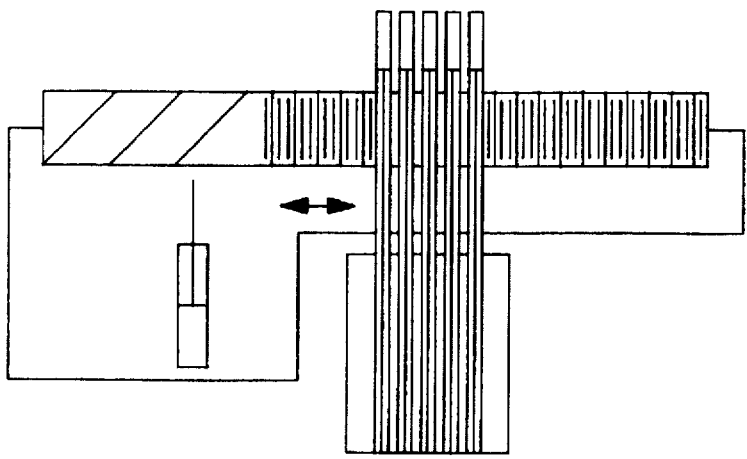

In FIG. 16 is a device for extracting several grafts in one operation from a skin piece. In the case shown, there are five grafts. The figure shows three situations where an assembling strip 22 carrying receptacles 3 is "run through" by five parallel-running cylindrical drill rods 26, all of them having a center rod 25. The drill rods are driven by the schematically indicated drill 27. In situation 16(a) the drill-out operation through the skin piece takes place, and hair roots or grafts fill the forward part of all five drill rods. In situation 16(b) the drill rods are about to be retracted after the drilling operation, and in situation 16(c) all five drill rods 26 have been retracted, while the center rods 25 have taken care of retaining all five grafts in their places in the five receptacles. Thereafter, the assembling strip is stepped five receptacle locations ahead, and the operation is repeated after having relatively moved the frame with the hair piece in a transverse direction, i.e. out of the paper plane, so that five new grafts can be extracted and placed in the five next receptacles. In this manner it is possible to execute a very rapid filling of an assembling strip. However, one will see that with the standardized intermediate gaps one loses at the same time the option of detailed control of where to extract grafts. However, due to the possible high speed of such an operation, this can be a very favorable solution anyway. In this case the computer is used to control a matrix-like movement across the whole skin patch. The number of drill rods and simultaneous grafts can of course be adapted such that one drills out grafts across the whole width of the skin piece in one drilling operation, and thereafter one moves in the longitudinal direction a suitably small distance, thereafter to drill out cylindrical grafts in a new transverse row.

Figure 16C:
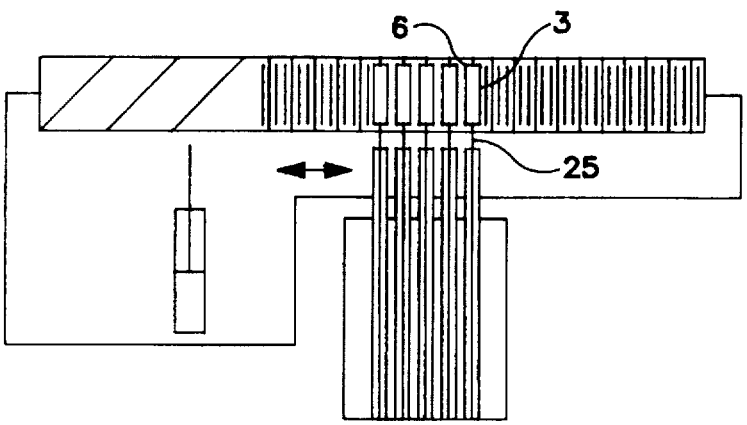

Moreover, it shall be noted that FIG. 16 can also be interpreted in an almost "opposite sense": a corresponding form of shooting in grafts can actually be executed, since the pistol which is mentioned substantially in the first part of the description can be widened out to comprise several points. One will then visualize a starting situation as indicated in FIG. 16c where the assembling strip 22 lies ready with filled receptacles 3, and a number of actuators of the previously described type starts advancing a corresponding number of points and receptacles for insertion into the patient's skin. The pistol will of course then have to be of a relatively complicated type. However, it will be possible to then obtain a very rapid execution of also this part of the operation.

Figure 17A:
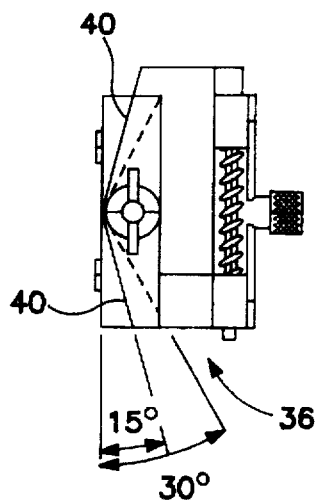

In FIGS. 17(a) and (b) are shown a frame 36 for mounting a cut-out skin patch 16 in a flat and taut manner. Important elements of the frame are two needle rows 37 comprising tilted needles along the edges of two plates 38. The skin patch 16 is threaded down onto the two needle rows along the edges of the skin patch, and thereafter the plates 38 are pulled apart by means of the tautening means 39 in such a manner that the skin piece then at the same time is tautened and pulled down to a position in a well defined plane flush with the plane of plate 38. One thereby avoids the problems for focusing the video camera, and the drilling operation can also be made more precise when the skin piece is mounted in a fixed and taut manner.

From the left part of FIG. 17(a) it is shown that the frame is equipped with an option for pivoting. This is because the hair roots in the skin piece 16 often lie at an angle in the skin, and one is interested in making the drilling-out operation as accurate as possible in the same direction as the longitudinal direction of the hair roots. A stop edge 40 for a maximum tilt position of 15° is shown, and a pivot angle of up to 30° is indicated by such an edge shown by a dashed line in the drawing.

Preferably the frame is also equipped with a cooling device, most preferably using cooled air, which by means of filters or other methods is purified with regard to polluting particles, and which can be guided exactly to the topical areas by means of controllable hoses. See for example FIG. 15, showing a cooling hose 321 for the skin patch 16 on the frame 32. A favorable temperature for the skin piece/hair roots is in the range about 4–5° C.

Finally it should be noted that research is being made these days regarding cloning (dividing) of the skin part of human hair (i. e. the part down in the skin) regarding the possibility of obtaining two hair growths from one single hair, i.e. one from the upper part and one from the lower part. See e.g. "Hair Transplant Forum", vol. 4, January-February 1994, page 19–20, Scott Friedman: "Hair cloning: Is the future here?". So far the experiments which have been conducted have been directed to transverse splitting of the skin part, and it is assumed that the actual regenerating process for hair takes place in an area located somewhat above the hair root itself.

By using a system in accordance with the present invention, where it is possible to cut out grafts or hair roots very precisely due to the monitoring and control by means of a computer, an opportunity will be provided for splitting the hairs longitudinally or in tilted incisions when the hairs are drilled out from the skin piece. When the hair is split longitudinally in such a manner, both of the cut pieces will have a larger contact area against the surrounding skin in the transplantation, and hence a larger possibility for survival and further growth.

Figure 17B:
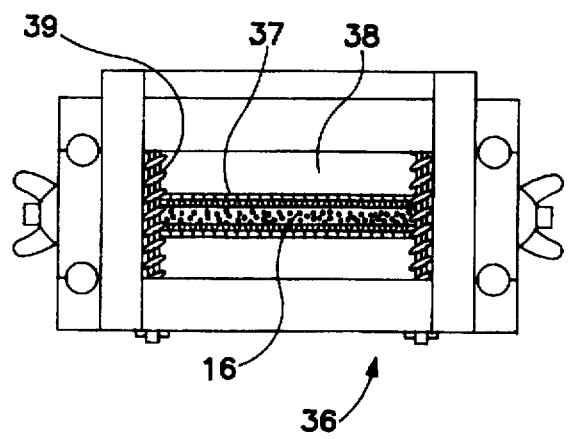

By means of the tiltable frame 36 shown in FIG. 17, as well as the precise control of the drill rod cutting in the skin piece, the cutting-out at one single hair can be regulated to any point on the hair stem between the actual root and the upper skin level in order to provide optimum effect for the purpose of cloning.

I claim:

1. A system for mechanical implantation of hair roots in skin by inserting skin grafts each comprising at least one hair root into the skin, said system comprising:
    a movable magazine;
    a means for extracting grafts from a piece of skin that has been surgically removed and placing the grafts in said movable magazine, said means for extracting and placing grafts comprising
        a frame for fixing and tautening the piece of skin,
        a cooling device for cooling the piece of skin, and
        a hollow drill rod for extracting the grafts from the piece of skin cooled by said cooling device and being movable to deliver the grafts to said magazine; and
    an implanting apparatus comprising an incision member and an actuator rod for successively conveying grafts from said movable magazine to an appropriate depth in the skin;
    wherein said implanting apparatus is configured such that said incision member and said actuator rod can successively and repeatedly make an incision in the skin, transversely widen the incision and insert a cooled graft from said magazine, and such that said magazine can be rapidly and automatically advanced in a stepwise manner in said implanting apparatus such that each graft in said magazine is maintained in a cooled state until inserted in the skin.

2. The system of claim 1, wherein said cooling device defines a means for cooling the piece of skin on said frame to a temperature where fat surrounding hair roots stiffens.

3. The system of claim 2, wherein said cooling device defines a means for cooling the piece of skin to 4–5 degrees C.

4. The system of claim 1, wherein said cooling device comprises at least one hose for supplying air to the piece of skin on said frame.

5. The system of claim 1, wherein said incision member comprises two adjacent knife edges that are capable of being rapidly and automatically advanced, split apart and retracted.

6. The system of claim 1, wherein said magazine comprises separate receptacles for each accommodating a graft, said receptacles being adapted to be advanced together with said actuator rod to be inserted into the skin while containing a graft therein together with said incision member and retracted prior to retraction of said actuator rod.

7. The system of claim 1, wherein said means for extracting and placing grafts further comprises a center rod inside said hollow drill rod adapted to leave each graft in said magazine by stopping the graft in said magazine while said drill rod is retracted therefrom.

8. The system of claim 1, wherein said frame is adjustable relative to said drill rod.

9. The system of claim 1, wherein said means for extracting and placing grafts comprises an automatic system for successive positioning of said drill rod relative to the piece of skin on said frame, said automatic system including a computer having a video input.

10. The system of claim 1, wherein said means for extracting and placing said grafts comprises an automatic system having a pre-programmed drilling pattern for successive positioning of said drill rod relative to the piece of skin on said frame.

11. A system for the mechanical implanting of hair roots in skin, comprising:
    a frame for holding a piece of skin in a fixed and taut manner;
    a cooling device positioned adjacent said frame for cooling the piece of skin;
    a movable magazine for holding skin grafts therein;
    a means for extracting the skin grafts from the piece of skin when the piece of skin is held in a fixed and taut manner by said frame and cooled by said cooling device and placing the skin grafts in said movable magazine, wherein said means for extracting and placing comprises a hollow drill rod that is movable to drill and extract the skin grafts from the piece of skin when the piece of skin is held by said frame and to deliver the skin grafts in to said magazine; and
    an implanting apparatus capable of receiving said movable magazine such that said movable magazine is stepwise advancable therein, said implanting apparatus comprising a means for successively implanting the skin grafts in said magazine into an appropriate depth in the skin, said means for implanting comprising
        an incision member capable of making an incision in the skin and transversely widening the incision in the skin such that the skin can receive one of the skin grafts, and
        an actuator rod for implanting the skin grafts in said movable magazine into the incision in the skin,
    whereby said magazine can be rapidly and automatically advanced stepwise by rapid and successive operation of said incision member and said actuator rod so as to maintain the skin grafts in said movable magazine in a cooled state until inserted into the skin.

12. A system for the mechanical implanting of hair roots into the skin, comprising:
    a movable magazine for receiving skin grafts;
    a skin graft extraction apparatus comprising
        a frame for holding a piece of skin in a fixed and taut manner,
        a cooling device positioned adjacent said frame for cooling the piece of skin, and
        a hollow drill rod that is movable between a position in which said drill rod can drill and extract skin grafts from the piece of skin when the piece of skin is held by said frame and a position in which said drill rod can deliver the skin grafts in to said magazine; and
    an implanting apparatus that is capable of receiving said movable magazine therein such that said movable magazine can be advanced stepwise therein and successively implanting the skin grafts in said magazine into an appropriate depth in the skin, said implanting apparatus including
        an incision member capable of making an incision in the skin and transversely widening the incision in the skin such that the skin can receive one of the skin grafts, and
        an actuator rod for implanting the skin grafts in said movable magazine into the incision in the skin,
    whereby said magazine can be rapidly and automatically advanced stepwise by rapid and successive operation of said incision member and said actuator rod so as to maintain the skin grafts in said movable magazine in a cooled state until inserted into the skin.

13. The system of claim 12, wherein said cooling device comprises a hose for supplying cooled air.

14. The system of claim 12, wherein said incision member comprises two knife edges that are movable between a first position in which said edges are together, and in which said position the incision into the skin is made, and a second position in which said edges are apart from each other so as to be able to transversely widen the incision into the skin.

15. The system of claim 14, wherein said movable magazine comprises a plurality of separate receptacles for holding respective skin grafts, said separate receptacles being capable of engaging said knife edges so as to move said knife edges between said first and second positions.

16. The system of claim 12, wherein said movable magazine comprises a plurality of separate receptacles for holding respective skin grafts capable of being inserted into the skin from said movable magazine so as to move a skin graft into the skin and retracted so as to leave the skin graft in said skin, and wherein said actuator rod is separately and independently movable through said separate receptacles so as to be capable of maintaining the skin graft in place in the skin upon retraction of said receptacles.

17. The system of claim 12, wherein said skin graft extraction apparatus comprises a means for relatively positioning said drill rod and the piece of skin held by said frame, a video camera and a computer connected to said video camera, said computer being connected to said means for relatively positioning.

18. The system of claim 12, wherein said frame comprises means for adjusting the alignment of said frame relative to drill rod.

19. The system of claim 12, wherein said skin graft extraction apparatus comprises a center rod inside said drill rod, said drill rod being longitudinally movable relative to said center rod.

20. The system of claim 12, wherein said skin graft extraction apparatus further comprises a means for automatically and successively positioning said drill rod relative to the piece of skin when the piece of skin is held by said frame so as to execute a pre-programmed drilling pattern.

* * * * *